United States Patent [19]
Elton et al.

[11] Patent Number: 4,571,695
[45] Date of Patent: Feb. 18, 1986

[54] NON-CONTACT ROAD PROFILOMETER AND DEFLECTION METER

[75] Inventors: David J. Elton; Milton E. Harr, both of West Lafayette, Ind.

[73] Assignee: Purdue Research Foundation, West Lafayette, Ind.

[21] Appl. No.: 396,618

[22] Filed: Jul. 9, 1982

[51] Int. Cl.⁴ .......................... G01B 3/18; G01B 5/00
[52] U.S. Cl. ...................................... 364/550; 33/551; 364/556
[58] Field of Search ............... 364/550, 554, 556, 559, 364/562; 356/356, 369, 371, 373, 376; 33/174 P, 174 R, 551–554; 73/104, 105

[56] References Cited

U.S. PATENT DOCUMENTS

| | | | |
|---|---|---|---|
| 3,151,235 | 9/1964 | Greenshields | 73/105 |
| 3,266,302 | 8/1966 | Spangler et al. | 73/105 |
| 3,888,118 | 6/1975 | Nims | 73/105 |
| 4,137,638 | 2/1979 | Watts . | |
| 4,231,160 | 11/1980 | Johnson et al. | 364/563 |
| 4,422,322 | 12/1983 | Spangler | 73/105 |
| 4,434,558 | 3/1984 | Face, Jr. et al. | 33/174 P |

FOREIGN PATENT DOCUMENTS 0078411  6/1982  European Pat. Off. ............ 364/376

Primary Examiner—James D. Thomas
Assistant Examiner—Dale M. Shaw
Attorney, Agent, or Firm—Barnes & Thornburg

[57] ABSTRACT

A pavement deflection measurement system is disclosed which continuously and simultaneously measures both a pavement profile and its deflection under load.

11 Claims, 2 Drawing Figures

DIRECTION OF MOTION

DIRECTION OF MOTION

NON-CONTACT ROAD PROFILOMETER AND DEFLECTION METER

FIELD OF THE INVENTION

This invention relates to a system, and apparatus and method for practice thereof, for measurement of the condition of a highway or airport runway surface, and is practiced by means of spaced laser measuring devices mounted on a rigid beam and used in combination with a computer controlled by a novel algorithm which, together, creates a survey profile of the surface traversed by the rigid beam.

BACKGROUND OF THE INVENTION

A. In General

The ability of airport pavement engineers to plan required maintenance on asphalt runways and taxiways is an increasing problem for which new, lower cost, solutions are needed. Because of the high cost of closing a runway of a commercial airport, the scheduling of maintenance is very important. This problem is accentuated by the increasing frequency of air travel and the weight of aircraft. Consequently, any system that will allow maintenance to be predicted and performed a complete failure takes place (requiring an unscheduled closing) would be most welcome.

At present, there exist several methods of testing asphalt pavements and of predicting when they will require maintenance. Generally speaking, these solutions all suffer from one or more of the following problems:

(1) very time consuming,
(2) can only test a few points on the pavement,
(3) requiring the destruction of a piece of the pavement in order to get the necessary parameters for prediction.

Obviously, the longer it takes to perform the test, the more expensive it will be.

B. Subjective and Objective Methods of Pavement Evaluation

1. Subjective Methods

The most common subjective measurement of pavement serviceability is the Present Serviceability Ratio (PSR). This method described by Yoder and Witczak (1975) entails driving over the pavement in question and rating it on a scale of 0 to 5 (very poor to very good). After a number of people have done this, the average of their ratings is taken and declared to be the PSR.

Related to the PSR is the Present Serviceability Index (PSI). The PSI is a number derived from a regression equation relating various pavement qualities (roughness, cracking, area of patching, etc.). It is used to derive results that agree with the PSR. Evaluation of the nature and extent of the parameters of the equation is somewhat subjective, making this method something less than exact. Nevertheless, both the PSI and PSR play useful roles in current pavement evaluation (Yoder and Witczak, 1975)

The PSI and PSR methods, being global, have the disadvantage of not being able to pinpoint problem areas. This makes repair more difficult. Another disadvantage of this method is the fact that it reflects variability due to human judgment.

No methods of subjectively evaluating the subgrade modulus of elasticity are known.

2. Objective Methods a. Introduction

Objective methods of measuring pavement deflection, roughness and texture and subgrade modulus abound. Most of the methods have been developed by highway engineers interested in measuring the strength of the pavement (as a measure of the remaining life), the rideability and/or the skid resistance. These methods usually involve a mechanical or electrical device that contacts the pavement and measures the desired quantity. Moreover, many of these devices require that the apparatus be stationary with respect to the pavement at the time of measurement, and thus yield data at only one location per set-up of the apparatus.

Four pavement parameters will be discussed (deflection, texture, roughness and subgrade modulus) on the basis of whether the particular test is destructive or nondestructive, contact or non-contact. Whether or not the test is continuous or discrete will be obvious from the description of the device.

b. Destructive tests—contact and non-contact

Destructive tests of asphalt pavements have been practiced for some time. One of the most popular is the California Bearing Ratio (CBR). This test entails pushing a standard cylinder into the base (or subbase or subgrade of a pavement) at a prescribed rate and measuring the resistance required to accomplish this task. This resistance is then correlated with laboratory tests or field performance data (Baker, 1975; Bowles, 1970). The results of the CBR test have been correlated with the modulus of elasticity of the subgrade by the following equation (Asphalt Institute, 1973; Yoder and Witczak, 1975)—

$$E = 1500\ CBR$$

where
E—modulus of elasticity (psi)

Yoder and Witczak, however, note that "Extreme caution should be exercised . . . when using this relation".

The modulus of elasticity of the subgrade can also be determined from the laboratory testing of a sample. The Asphalt Institute (1978) describes how to determine the "resilient modulus", which is defined as $$RM = \sigma_d / E_v$$

where
RM—resilient modulus
$\sigma_d$—deviator stress in triaxial cell
$E_v$—vertical strain of sample Other have described slightly more subjective ways to determine the modulus. The Asphalt Institute (1973) relates the FAA Soil Classification to the modulus, ranging from an F10 soil with a 5500 psi modulus to an Fa soil with 31,000 psi modulus. Kezdi (1975) gives approximate ranges of the modulus for different soils and conditions. His values range from 50–400 psi for very soft clays to 14,000–28,000 psi for dense sand and gravel.

The plate bearing test is another common destructive test used to evaluate soil beneath the pavement. It consists of digging a pit large enough to accommodate the plate, and loading it while measuring the corresponding settlement. Usually it is run to determine the modulus of subgrade reaction, which is used in the analysis of the pavement system. The general procedure is described by Yoder and Witczak (1975). McLeod (1957), used the plate load test to determine a relation between deflection and settlement. Often this test is run before the roadway is constructed so that the proper thicknesses of base, subbases and surface courses can be computed.

Vesic and Saxena (1970) studied rigid pavements and the effect of subgrade reaction on the AASHO Road Test pavements. They found that it was very difficult to find a single value of the modulus that would predict deflection, shear stresses, moments and contact pressures at the same time. They noted that the modulus was a function of how the test was run and the size of the plate used. For shallow depth subgrades (i.e. those with bedrock near the surface), they were able to get a single value that satisfied all the statical parameters (deflection, moments, etc.).

Terzaghi, in 1955, also noted that the modulus of subgrade reaction varied with the width of the plate (or footing) resting on the soil.

These above noted methods have been developed primarily for highway use. While they are common tests for design, they are not common tests for pavement evaluation. This is because they are expensive, time consuming and interfere with traffic. Other, more conventional, methods of testing the soil below the pavement exist (these belong to the province of soil mechanics; the interested reader is referred to Terzaghi and Peck (1967)). All conventional methods of soil testing require a sample, and thus are destructive.

There are no destructive non-contact methods of pavement evaluation known to applicants.

c. Non-destructive tests—Contact and Non-Contact

1. Deflection

Deflection of the surface of a pavement under load is the most obvious non-destructive method of evaluating the adequacy of a pavement. Many different apparatuses have been developed to measure pavement deflections.

Probably the most widely used (and widely acclaimed) device is the Benkelman beam (Yoder and Witczak (1975)).

The advantages of the Benkelman device (which probably account for its popularity) are its ease of use, simplicity of construction and its durability. The disadvantages are the length of time it takes to set up, the fact that only one deflection measurement is made at each site, deflection beneath the tire cannot be measured, and that the rebound of the pavement is measured instead of the deflection caused by a moving wheel load.

2. Texture

Surface texture of pavements is of interest to the highway or airport engineer who desires to evaluate the skid resistance or hydroplaning potential of a pavement. Hydroplaning potential is a measure of how well the pavement drains.

Surface texture of asphalt pavements is most commonly measured by contact methods. Rose, Hutchinson and Galloway (1973) provide an interesting review of methods that have been used. They cite the following methods—

(1) The "patch" method—rub a given quantity of some substance onto the surface of the road until it forms an approximately circular area whose surface is at the height of the projections of the asphalt aggregate. The diameter of the circle is a measure of roughness (large diameter implies smooth texture). Materials used include sand, grease and silicone putty.

(2) The direct measurement method—This consists, usually, of drawing a feeler needle across the surface and watching its variation in height. Large variation in needle height implies rough texture (also ref. Goodman (1970) and Moore (1966)).

(3) Miscellaneous methods—

(a) lay a piece of metal foil on the pavement, strike it with a standard rubber mallet and count the number of holes made in the foil. This method has the advantage of finding the sharp points, which are not distinguished by the former methods.

(b) Make a plastic cast of the surface, smear it with paint and measure the percent of area that took paint.

3. Roughness

Pavement roughness is of interest to engineers concerned with the pavement users comfort and safety. Rough pavements make vehicle control difficult and the ride uncomfortable. At present there are two basic methods of measuring roughness—(1) quantifying the change in the pavement profile (either locally or globally) and, (2) measuring vehicle accelerations caused by the changes in profile. Of the two, the former is more common.

(4) Modulus of elasticity of the subgrade

Deflections can be used to evaluate the modulus of elasticity of the subgrade. This has been done using vibrators, such as the Shell and Road Rater models. Cunny and Fry (1973) gave a brief description of how the vibrator methodology works.

They note that the properties thus derived apply best to soils at depths of $\lambda/2$.

Weiss (1977), working with the Waterways Experiment Station vibrator, proposes two methods of determining the modulus. The first, called the "dynamic frequency response spectrum method", models the soil with a mass, spring and dashpot. By using the amplitudes of the waves produced by the vibrator, the properties of the model are determined. It is an iterative process. Once gotten, these properties are used in the Chevron layered elastic computer program to calculate the modulus. The moduli of the pavement and base courses also must be known before the Chevron program can be run. The results of this method do not compare well with the $E=1500$ CBR equation. The derived moduli are consistently larger.

The second method Weiss proposes is the dynamic load-deflection curve method. Briefly, this method entails using a non-linear dynamic response theory that, given a subgrade modulus and pavement moduli, predicts surface deflections. When the measured surface deflections agree with the predicted ones, the correct modulus has been chosen. The results of this method generally agree with the $E=1500$ CBR formula.

There are a great number of ways to test pavements available to the pavement engineer. The divergence of opinion on the subject reflects not only the uncertainty of present methods, but also the need to account for regional factors. This invention proposes a method and apparatus whereby many of these regional factors are accounted for. Further, its purpose is to provide pavement engineers with a rapid, non-destructive method of evaluating pavements so that maintenance costs can be reduced.

SUMMARY OF THE INVENTION

The method and apparatus of this invention are shown in FIG. 1. FIG. 1 shows a load vehicle (here a truck) carrying the system that will analyze the pavement condition. The system consists of four laser distance measuring gages attached to a rigid beam which, in turn, is attached to the side of the load vehicle. The purpose is to quantify a deflection created by the load wheel. As the vehicle traverses the runway, at specified intervals (determined by the fifth wheel) the gages measure the distance to the pavement.

In the process of measuring the deflection, two other important pavement characteristics are measured: the undeflected profile and the surface texture. The texture measurement is made possible because the gages have a resolution smaller than the particle size of asphalt pavement and because a large number of values can be had in the near vicinity of a point on the pavement. The profile can be used in determining the roughness of the runway.

The proposed system is quick, versatile, requires no mechanical contact with the pavement surface, and uses actual wheel loads. It allows the operator to test the pavement in a global sense, and at any time of the day. The accompanying electronics, while very sophisticated, are easy to use. With some training, maintenance personnel can operate it. Almost any vehicle that the beam can be attached to can serve as the load vehicle—trucks, cars, airplanes, fire engines—any vehicle that produces a measurable deflection can be used.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

The main components of the system are the electro-optical distance measuring gages, a rigid beam, a fifth wheel, and the attendant electronics.

Figure 1:
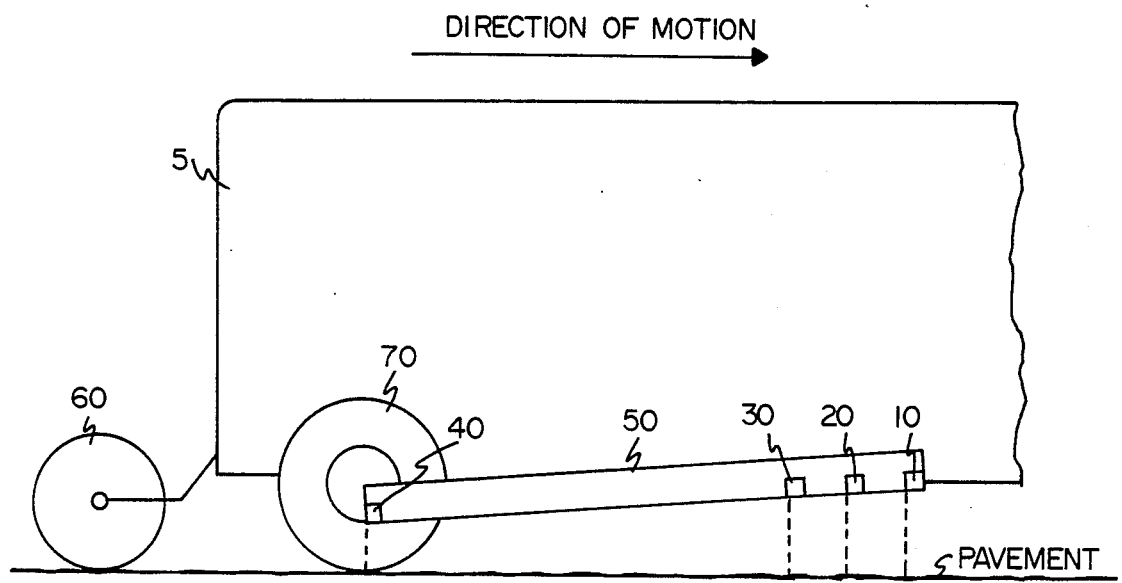
FIG. 1 shows a diagrammatic view of the system.

The electro-optical distance measuring gages 10, 20, 30, and 40 are mounted on a rigid beam 50 which in turn is mounted longitudinally on a load vehicle 5 (see FIG. 1). The gage heads measure the distance from the beam to the pavement in a non-contact way (using lasers). Acoustic wave measurement devices could also be used with suitable changes in the software.

The rigid beam 50 on which the gages are mounted is an important part of the system. In order for the data analysis system to work, the gages cannot move relative to their original alignment. For this reason, they are mounted on a rigid beam.

The data analysis system requires each gage to read the distance from the rigid beam to the pavement surface at the same (in the statistical sense) horizontal locations. Each succeeding gage must read where the preceding gages have read. A distance measuring device is required to set the time when the gages should read. A fifth wheel 60 is used to provide this measure. The speed of the vehicle is determined, indirectly, from the fifth wheel.

The attendant electronics (standard, but not shown) are the power supply, computer, and the electronics for the fifth wheel.

1. Theory for Profile, Deflection and Texture Measurement

The deflected profile of the pavement adjacent to the wheel load is measured as well as the undeflected profile. The algorithm that provides necessary control over the hardware here proposed is hereafter described.

Figure 2:
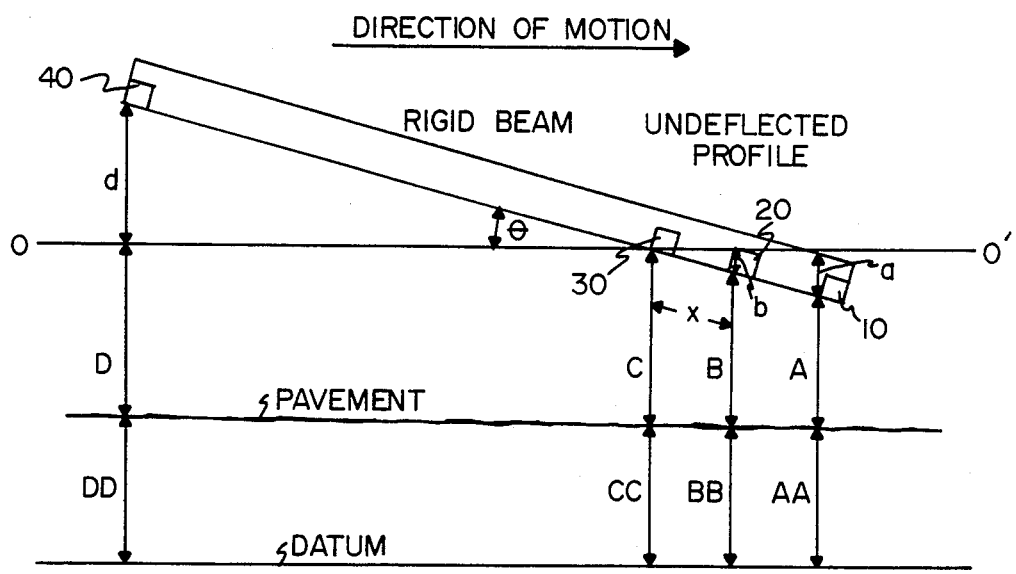
FIG. 2 is a schematic, graphic, view of the system.

The algorithm that determines the undeflected profile of the pavement uses five values—three gage measurements and two arbitrary elevations above a datum. These five inputs are used to calculate a new elevation above the datum while the vehicle moves to a new location. In FIG. 2, the two known elevations are designated as BB and CC, and the three gage head measurements are A, B, and C. Given these five inputs, the algorithm calculates a new elevation, AA, in front of the known elevations. All five inputs are had from the undeflected portion of the pavement. AA defines a point on the undeflected profile. For this reason, the front three gages 10, 20 and 30 are collectively called the "undeflected profilometer". When elevations are determined in the area influenced by the wheel load (exerted through load wheel 70), deflected profile points are calculated. As any five inputs may be used, (if chosen in a manner consistent with that just described), the elevation can be calculated at gage 40, near the load wheel.

The derivation of the algorithm follows from FIG. 2. Here, as above, BB and CC are arbitrary, and A, B, and C are obtained as readings from the gages.

Note that, because 00' is constructed parallel to the datum, $$C+CC=B+BB+b=A+AA+a \qquad (1)$$

C, B, and A are known. If the gages are evenly spaced on the beam $$a=2b \qquad (2)$$

Noting this, and $$b=C+CC-B-BB \qquad (3)$$

gives (by substitution)

$$AA=C+CC-A-2*(C+CC-B-BB), \qquad (4)$$

which is the desired quantity, the new undeflected elevation. AA can be calculated from (4) as all the quantitives on the right side of the equation are known (either measured or defined). The process is repeated in this way—the gages move forward until gage 20 is over the previous position of gage 10 (in the statistical sense), and the algorithm is repeated, using the five new quantities (BB being the previous AA, and CC being the previous BB). A new undeflected profile point is then calculated. Extended repetition eventually yields the entire undeflected profile at increments corresponding to the gage spacing.

The spacing of the gages on the beam is very important. By mounting all the gage heads at equal intervals along the beam, the gage head readings can be timed so that each reads at the same location as the previous one. Thus, any three gages can be used as a profilometer. By placing gage 40 an integral number of gage spacings from gages 10, 20, and 30, gages 20, 30, and 40 can be used as a profilometer. Whereas AA was calculated in a "forward" manner, DD is calculated in a "backward" manner. The five inputs are B, C, D, BB, and CC. DD is calculated from $$DD=C+CC-D+(r)(C+CC-B-BB) \qquad (5)$$

where r is the ratio of the distance between gages C and D to the distance between gages B and C. When the B-C-D profilometer is used, the deflected profile is calculated, gage D being near the load wheel.

The deflection (relative to the undeflected profile) caused by the load wheel can now be calculated. The undeflected profile was calculated by the A-B-C profilometer. The deflected profile was calculated by the B-C-D profilometer. The fifth wheel assures that all gages read at the exact (in the statistical sense) same points on the pavement. So, two profiles are had. The difference between the two is the deflection caused by the load wheel.

From the measurements described above, two important pavement parameters can be ascertained—the roughness (profile), and the deflection adjacent to the wheel. Because the gages can make measurements at a very rapid rate (16 kHz), another important pavement characteristic—the pavement texture—can be determined. The texture can be had from the variations in readings in the near vicinity of a point on the pavement. This variation is possible because light spot size is much smaller than the variation in the surface texture.

Many readings are required over a short distance not only so that the texture can be measured, but also to keep null readings due to drop-out from entering the profile algorithm. Drop-outs occur when the light spot from the gage is hidden from the view of the photodetector. In order to keep from losing the data point, the gage head makes many readings over a short distance, averages them, and considers the average to be the distance to the center of the short distance. Four inches is the short distance in this study.

Averaging many readings provides a very stable statistical measure of the distance from the gage to the pavement. The large number of readings allows an extra order of magnitude to be added to the accuracy.

Because the resolution of the gages is much smaller than the variation in the surface texture, the variations in the readings over four inches of pavement reflect the courseness of the surface of the pavement. A large variation indicates a coarse surface, while a small variation indicates a smooth one. A useful measure of the variation in the readings is the statistical variance (V)—

$$V = \sum_{i=1}^{n} (x_i - \bar{x})^2/(n-1) \quad (6)$$

As an alternative to using three gages for the profilometer, two gages and a tiltmeter (not shown) can be used. A tiltmeter is an electro-mechanical device that measures the angle of a surface with respect to a level datum.

The algorithm for finding the profile is similar to that used with three gages. Consider FIG. 2 again. This time, gages 20 and 30 will be used. The inclination of the beam is $\theta$. Initially, B, C, and CC are known. CC was chosen to define the datum—the datum being level and passing through the end of CC, with x known, $$b = x \sin \theta \quad (1)$$

$$B + b + BB = C + CC \quad (2)$$

so, $$BB = C + CC - B - b \quad (3)$$

substituting (1) into (3) yields $$BB = C + CC - B - (x \sin \theta) \quad (4)$$

Note that the terms on the right side of the equation are known. Thus, the next pavement profile point is had. The beam moves forward, as before, until gage C is over where gage B was, and the process is repeated. The method can be used with gage 30 and 40 to get the deflected profile.

The deflection and texture measurements can be calculated in the same manner described above.

The speed and location of the vehicle during a test are recorded with each profile/deflection measurement. By knowing the frequency of the readings (16 kHz), the number of readings (n), and the distance over which the readings were taken (four inches), the speed can be had from $$\text{speed} = (4)(16000)/n \quad \text{inches/second} \quad (7)$$

An alternate method also was used to calculate the speed. The time to traverse four inches was measured by a clock in the computer which ran the data collection program. By dividing the four inch measurement by this time, the speed was had.

Gage readings were made every foot, over the four inch distance. That is, the gages would read for four inches, skip eight inches, read for another four inches, etc. As the readings are one foot apart, counting the number of readings gives the distance travelled in feet. Thus, the location is secured.

In order for the profile algorithm described above to work, the gages must remain fixed in space relative to each other. As this system is to be used with almost any load vehicle, attaching the gages rigidly to the load vehicle is unacceptable. Attaching the gages to a rigid, portable beam provides the necessary flexibility.

The length of the beam is important. The beam must be long enough to hold one gage 40 near the load wheel, and to hold the undeflected profilometer (gages 10, 20, 30) outside the zone of influence of the load wheel. A ten foot beam (nine feet between gages) does this.

The beam must be stiff enough to restrain the gages from moving out of their original alignment. The allowable movement is the resolution of the gages. Any greater movement does not allow determination of whether the pavement had deflected or the beam had moved.

In operation, the data acquisition system collects the data generated by the lasers and the fifth wheel. It consists of a microcomputer and various peripherals. The computer is triggered by the pulses from the fifth wheel. When the fifth wheel gives the proper pulse, the computer clock is started, and the computer begins 'looking at' the readings from the lasers. It averages the readings from each gage, and computes standard deviations for all of them. When the fifth wheel sends the next pulse, the clock stops, the computer stops looking at the readings, and the data is put in core memory. When the desired pavement has been traversed, the operator flips a logic switch which tells the computer to stop the data gathering program. The program stops and the data is written onto a floppy disc. These data are then used by the profile/deflection program.

For ease of description, the term "system software" will be used to describe standard software not claimed as part of the present invention. "User software" is that written by the applicants and that which embodies the novel algorithm which forms an integral part of the claimed invention.

System software included a FORTRAN IV compiler, editor, linker, library functions, assembly language compiler, and a file manager. User software included a data gathering program (GATHER), a data file previewer (LIST), and the data reduction program (CALC).

Describing the "system software" functions is best done by tracing typical steps in the program creation and execution process. A program is written and modified in the editor. When it is correct, it is compiled by the computer. Then it is linked to the library files by the linker. Then, if no errors are found, the program can be run. Should the program be written in assembly language, the assembly language compiler is substituted for the FORTRAN IV compiler. The file manager is used to view, compress, and copy files.

GATHER was written in assembly language so it would be fast enough to keep up with the lasers. When GATHER is run, it asks the operator to name the data to be gathered. After accepting this, GATHER prompts the operator to flip the start switch on the logic box. This being done, GATHER monitors the fifth wheel shaft encoder, the logic box, the line time clock on the computer and the four laser gages. The fifth wheel encoder gives a pulse every four inches of travel over the pavement. GATHER checks the pulse frequently, and counts the pulses. The beginning of the pulse representing the first four inches of every foot tells GATHER to begin reading, counting and averaging the readings from the lasers. At the same time, it begins counting 1/60-ths of a second on the line time clock. It also beings calculating standard deviations of all four of the lasers. Later, the time is used to calculate speed. While doing this, the computer checks the pulse to see if four inches of pavement have been traversed. When the pulse changes, the four inches have passed, and GATHER puts the four average readings, the number of 1/60-ths of a second, and the four standard deviations into memory. When the operator flips the start logic switch to stop, GATHER puts values of negative one in for all the readings, puts them in memory, and writes the entire data set onto the disc under the name the operator assigned. The negative ones signal the end of the data to the data reduction program.

After the data is gathered, the operator may wish to preview the data before reducing it. Of interest are the number of readings, the number of zero readings, the standard deviations, and the length of the file. The user program LIST enabled the operator to do these things.

The averaged laser readings are converted to profile and deflection measurements by the user program CALC. CALC reads the data from the file created by GATHER. It then uses all the data to get two constants—the two out-of-line measurements of gages 10 and 40.

Recall that, for the algorithm to work, the gages must be in a straight line. Gages 20 and 30 define the line. CALC can calculate how far out of line gage 10 is any time, and how far out of line gage 40 is if the pavement is undeflected.

This is accomplished as follows (based upon the assumption that the gages do not move relative to one another, and that their relative positions are known).

Referring to FIG. 2, let i be one step in the direction of motion. Note that—

$$AA_i = BB_{i+1} = CC_{i+2} \quad (1)$$

For n (large number) we get (approximately):

$$\sum_{i=1}^{n} AA_i = \sum_{i=1}^{n} BB_i = \sum_{i=1}^{n} CC_i \quad (2)$$

Note that, at any time, the two endpoints of each of the scaler quantities A+AA, B+BB, and C+CC should define two straight lines (the datum and the rigid beam). Therefore, the two endpoints of each of the scalar quantities of $$\sum_{i=1}^{n} (A_i + AA_i), \sum_{i=1}^{n} (B_i + BB_i) \text{ and } \sum_{i=1}^{n} (C_i + CC_i) \quad (3)$$

also form two straight lines.

Because of (2), it can be said that one endpoint of each of the three following scalar quantities $$\sum_{i=1}^{n} (A_i + AA_i) - \sum_{i=1}^{n} (AA_i) \quad (4)$$

$$\sum_{i=1}^{n} (B_i + BB_i) - \sum_{i=1}^{n} (BB_i) \quad (5)$$

$$\sum_{i=1}^{n} (C_i + CC_i) - \sum_{i=1}^{n} (CC_i) \quad (6)$$

nearly form a straight line.

Rewriting (4), (5), and (6) give (the averages):

$$\frac{\Sigma A}{n} = \bar{A}, \frac{\Sigma B}{n} = \bar{B}, \frac{\Sigma C}{n} = \bar{C} \quad (7)$$

whose endpoints also form nearly a straight line.

When a test is run, the beam alignment constant can be determined if the sums at (7) are had.

The averages should represent two nearly straight lines. If they don't, the difference between one average and the straight lines formed by the other averages is the amount that that gage is out of line with the other two gages. That difference (the out-of-line constant) should be added to the calibration equation for that gage (the effect is to remove a constant offset from that gage).

This method can be extended to the D gage, if the pavement is not deflected. A light tricycle was used for this purpose. It carried the beam without significantly loading the pavement. The tricycle was pulled by hand.

The out-of-line constants for gages 10 and 40 are determined automatically by the computer program CALC.

These two constants are then added to their respective calibration equations to correct the out-of-lineness. CALC then rereads the data, this time using constants derived from the novel algorithm described above to obtain the profile and deflections. Then, if the operator desires, plots of the profile vs. distance and deflection vs. distance are produced.

Occasionally, null readings occur. The effect of a null reading on the algorithm depends on when the null occurs, and at which gage it occurs.

A special condition occurs when a test is started. The first seven feet of travel (the distance between gages 30 and 40) is a special zone at this time. No deflections are measured here, as the undeflected profile has not been measured there. Consequently, if gage 40 produces a null here, it has no consequnece. If gage 10, 20, or 30 produce a null (or any combination of nulls) in this zone, CALC ignores past data and begins the algorithm afresh. This happens because the algorithm cannot tolerate any gaps in the continuity of the data.

After the first seven feet are past, deflections are calculated. The profile continues to be calculated. If gage 10 produces a null, a deflection is calculated, and the profile is ended. At the next reading, a new profile is begun. Six deflections are lost (those between gages 30 and 40). The algorithm begins anew as described in the last paragraph. If gages 20 or 30, or both, produce a null, no deflection is calculated, the profile ends, and then begins anew at the next reading. Seven deflections are lost. The CALC program performs all these operations automatically.

There are two ways to create a null reading. First, the pavement may move out of range of the gage. The gage then returns a null reading to the computer. Second, the gage may make less than thirty readings in the four inch span. This is interpreted as the gage having gone out of range part way through the four inches. CALC interprets this as a null. The CALC program detects both cases.

The CALC program puts out the following information.
1. the distance travelled,
2. the number of null readings at each gage,
3. the two out-of-line constants,
4. the undeflected profile,
5. the deflections, their mean and standard deviation,
6. a measure of the texture, and
7. plots of the deflected profile or deflections versus distance.

Other expedients to accomplish the invention described above may be apparent to those skilled in the art, but the scope of applicants' invention is to be limited only by the scope of the appended claims.

What is claimed is:

1. An apparatus for continuously measuring a road surface profile, the apparatus comprising
 a rigid frame attached to a vehicle,
 first, second, and third profile detecting means, serially mounted on the rigid frame in spaced-apart relation, for measuring a distance between a selected datum line on the frame and the underlying road surface,
 control means for simultaneously instructing the first, second, and third profile detecting means to activate to cause the distance to be simultaneously measured between the selected frame datum and the underlying road surface at three laterally spaced-apart locations to provide a set of distance data,
 sequencing means for periodically activating the control means,
 data collection means for sequentially recording a plurality of the sets of distance data periodically measured by the first, second, and third profile detecting means, and
 computer means for manipulating each of the sets of distance data recorded by the data collection means to mathematically compute the profile of the underlying road surface.

2. The apparatus of claim 1 wherein each profile detecting means includes one of an electro-optical distance measuring gage and an acoustic wave measurement device.

3. The apparatus of claim 1 wherein the sequencing means includes
 a fifth wheel means, coupled to the vehicle, for measuring the distance traveled by the vehicle along the road surface by substantially maintaining contact with the underlying road surface, and
 processor means for activating the control means at selected intervals as a function of the distance measured by the fifth wheel means such that the second profile detecting means measures a distance during one of the selected intervals at substantially the same location on the underlying road surface that the first profile detecting means measured a distance during an interval immediately preceding the one of the selected intervals and such that the third profile detecting means measures a distance during the one of the selected intervals at substantially the same location on the underlying road surface that the second profile detecting means measured a distance during the interval immediately preceding the one of the selected intervals.

4. The apparatus of claim 1 wherein the vehicle includes a load-transmitting wheel or the like that maintains substantial contact with the road surface, and wherein each of the first, second, and third profile detecting means are mounted on the rigid frame to lie a predetermined distance away from the load-transmitting wheel such that the distances measured by the three profile detecting means are not substantially varied due to deflection of the road surface caused by the load-transmitting wheel whereby an undeflected profile of the road surface is generally defined by the plurality of sets of distance data provided by the three profile detecting means.

5. The apparatus of claim 4 wherein the three profile detecting means are substantially equally spaced apart along the rigid frame.

6. The apparatus of claim 1 wherein the vehicle includes a load-transmitting wheel or the like that maintains substantial contact with the road surface, and wherein the first profile detecting means is mounted on the rigid frame in proximity to the load-transmitting wheel, the second and third profile detecting means are mounted on the rigid frame to lie a predetermined distance away from the load-transmitting wheel such that the distances measured by the second and third profile detecting means are not substantially varied due to deflection of the road surface caused by the load-transmitting wheel whereby a deflected profile of the road surface is generally defined by the plurality of sets of distance data provided by the three profile detecting means.

7. The apparatus of claim 6 wherein the first and second profile detecting means are separated by a first lateral distance, the second and third profile detecting means are separated by a second lateral distance, and the first lateral distance is greater than the second lateral distance.

8. A method of continuously collecting a stream of data indicative of a profile of a road surface, the method comprising the steps of
 providing a plurality of distance measuring gages in fixed spaced relationship upon a rigid beam, a first of the gages being positioned in proximity to a means for loading a road surface underlying the plurality of gages, each of the gages other than the first gage being fixed on the rigid beam to lie a selected distance away from the loading means, measuring the distance from each of the gages other than the first gage to the underlying road surface, advancing the rigid beam in relation to the underlying road surface to cause the gages to be positioned substantially above the underlying road surface at a point at which another of the gages had been previously positioned, and concurrently with the advancing step, recording the distances measured by each of the measuring gages to provide a set of distance data indicative of one of an undeflected profile and a deflected profile of the underlying road surface.

9. The method of claim 8 further comprising the steps of (a) selecting two known elevations above a datum reference underlying the road surface, (b) calculating the undeflected profile of the road surface as the rigid beam is advanced thereabove according to the following algorithm:

$$AA = C + CC - A - \frac{(AB + BC)}{BC}(C + CC - B - BB)$$

wherein A, B and C are the distances measured from the said other gages to the undeflected road surface, and BB and CC are known elevations measured along a line extended from the B and C distances to the reference datum, and where AB and BC are the distances between the gages producing measurements A and B, and B and C, respectively, (c) repeating a series of steps (a) and (b), and (d) plotting the undeflected profile.

10. The method of claim 8 further comprising the steps of (a) selecting two known elevations above a datum reference underlying the road surface, (b) calculating the deflected profile of the road surface as the rigid beam is advanced thereabove according to the following algorithm:

$$DD = C + CC - D + (r)(C + CC - B - BB)$$

wherein B and C are the distances measured from two of the said other gages to the road surface, D is the distance measured to the road surface by one of the gages fixed in proximity to the loading means, r is the ratio of the lateral distance between the gages measuring C and D to the lateral distance between the gages measuring B and C, (c) repeating a series of steps (a) and (b), and (d) plotting the deflected profile of the road surface.

11. The method of claim 9 further comprising the steps of (e) calculating the deflected profile of the road surface as the rigid beam is advanced thereabove according to the following algorithm:

$$DD = C + CC - D + (r)(C + CC - B - BB)$$

wherein B and C are the distances measured from two of the said other gages to the road surface, D is the distance measured to the road surface by one of the gages fixed in proximity to the loading means, r is the ratio of the lateral distance between the two gages measuring C and D to the lateral distance between the two gages measuring B and C, (f) repeating a series of step (a) of claim 8 and step (e) of claim 10 such that the deflected profile of the road surface is plotted, and subsequently (g) calculating the deflection of the road surface caused by the load imposed upon the road surface by computing the differences between the said undeflected profile and the said deflected profile.

* * * * *

UNITED STATES PATENT AND TRADEMARK OFFICE
CERTIFICATE OF CORRECTION

PATENT NO. : 4,571,695
DATED : February 18, 1986
INVENTOR(S) : David J. Elton and Milton E. Harr It is certified that error appears in the above-identified patent and that said Letters Patent is hereby corrected as shown below:

Column 1, line 13, after "beam", insert --The Federal Government may have rights in this invention due to sponsorship by the FAA (DOT).--.

Column 9, line 35, change "beings" to --begins--.

Column 11, line 4, change "consequnece" to --consequence--.

Column 14, line 32 (claim 11), change "8" to --9--.

Column 14, line 33 (claim 11), change "10" to --11--.

Signed and Sealed this

Twenty-ninth Day of July 1986

[SEAL]

Attest:

DONALD J. QUIGG

Attesting Officer    Commissioner of Patents and Trademarks